United States Patent
Doetz et al.

(10) Patent No.: US 7,906,225 B2
(45) Date of Patent: Mar. 15, 2011

(54) SYNTHESIS OF PHENYL-SUBSTITUTED FLUORANTHENES BY A DIESEL-ALDER AND THE USE THEREOF

(75) Inventors: Florian Doetz, Heidelberg (DE); Reinhold Schwalm, Wachenheim (DE); Joachim Roesch, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 698 days.

(21) Appl. No.: 10/573,803

(22) PCT Filed: Sep. 28, 2004

(86) PCT No.: PCT/EP2004/010850
§ 371 (c)(1),
(2), (4) Date: Mar. 28, 2006

(87) PCT Pub. No.: WO2005/033051
PCT Pub. Date: Apr. 14, 2005

(65) Prior Publication Data
US 2007/0069198 A1 Mar. 29, 2007

(30) Foreign Application Priority Data
Sep. 29, 2003 (DE) ................. 103 45 583

(51) Int. Cl.
*H01L 51/54* (2006.01)
*C09K 11/06* (2006.01)

(52) U.S. Cl. ........ 428/690; 428/917; 313/504; 313/506; 257/40; 257/102; 257/103; 257/E51.049; 252/301.16; 528/220

(58) Field of Classification Search .................. 428/690, 428/917; 427/58, 66; 313/502–509; 257/40, 257/E51.001–E51.052, 88–103; 252/301.16–301.35
See application file for complete search history.

(56) References Cited

U.S. PATENT DOCUMENTS

| 5,281,489 A | 1/1994 | Mori et al. |
|---|---|---|
| 2001/0004190 A1* | 6/2001 | Nishi et al. ............. 313/506 |
| 2002/0022151 A1 | 2/2002 | Ishikawa et al. |
| 2003/0054200 A1* | 3/2003 | Tagami et al. ............. 428/690 |
| 2005/0067955 A1* | 3/2005 | Cho et al. ............. 313/510 |

FOREIGN PATENT DOCUMENTS

| EP | 1 138 745 | | 10/2001 |
|---|---|---|---|
| JP | H10-189248 A | * | 7/1998 |
| JP | 2000-007587 | | 1/2000 |
| JP | 2001-257075 | | 9/2001 |
| JP | 2002-069044 A | * | 3/2002 |

OTHER PUBLICATIONS

Williams, et al., "Characterization of Unsaturated Compounds by means of acycyclone," Makromolekulare Chemie, vol. 82, pp. 281-283, 1965.*
Machine translation of JP 2002-069044 A (2002).*
Wu et al. "From branched hydrocarbon propellers to C3-symmetric graphite disks." J. Org. Chem. 2004, vol. 69, pp. 5179-5186.*
Machine translation of JP H10-189248 A.*
Ghosh et al. "Synthesis of Arylated Fluoranthene Derivatives." Indian J. Chem. vol. 16B, 1978, pp. 152 and 153.*
Bernius, Mark T. et al., "Progress with light-emitting polymers", Advanced Materials, vol. 12, No. 23, pp. 1737-1750, 2000.
Dilthey, Walther et al., Hocharylierte aromatische Verbindungen (VI. Mitteil.), Chem. Ber. vol. 71, No. 5, pp. 974-979, 1938.
Allen C.F.H. et al., "Addition Reactions of Vinyl Phenyl Ketone. VI. The Diene Synthesis", J. Am. Chem. Soc., vol. 62, pp. 656-664, 1940.

* cited by examiner

Primary Examiner — D. Lawrence Tarazano
Assistant Examiner — Michael Wilson
(74) Attorney, Agent, or Firm — Oblon, Spivak, McClelland, Maier & Neustadt, L.L.P.

(57) ABSTRACT

A substituted fluoranthene, a light emitting layer including the substituted fluoranthene, a diode including the substituted fluoranthene, and a visual display unit including the substituted fluoranthene.

18 Claims, No Drawings

SYNTHESIS OF PHENYL-SUBSTITUTED FLUORANTHENES BY A DIESEL-ALDER AND THE USE THEREOF

The present invention relates to fluoranthene derivatives, a process for preparing them and the use of fluoranthene derivatives as emitter molecules in organic light-emitting diodes (OLEDs), a light-emitting layer comprising the fluoranthene derivatives of the invention as emitter molecules, an OLED comprising the light-emitting layer of the invention and devices comprising the OLED of the invention.

Organic light-emitting diodes (OLEDs) exploit the ability of particular materials to emit light when they are excited by an electric current. OLEDs are of particular interest as alternatives to cathode ray tubes and liquid crystal displays for producing flat VDUs.

Numerous materials which emit light on excitation by an electric current have been proposed.

An overview of organic light-emitting diodes is disclosed, for example, in M. T. Bernius et al., Adv. Mat. 2000, 12, 1737. The compounds used have to meet demanding requirements and the known materials are usually not able to meet all the demands made.

U.S. Pat. No. 5,281,489 discloses OLEDs which can comprise, inter alia, 3,4-benzofluoranthene or monomeric unsubstituted fluoranthene as fluorescent materials. However, monomeric unsubstituted fluoranthene can migrate under the conditions prevailing in OLEDs during use. The layer of monomeric unsubstituted fluoranthene is not stable, resulting in a short life of the diodes.

The use of specific fluoranthene derivatives is disclosed in US 2002/0022151 A1 and EP-A 1 138 745.

EP-A 1 138 745 relates to an OLED which emits reddish light. This OLED comprises an organic layer comprising a compound having a fluoranthene skeleton, with the fluoranthene skeleton being substituted by at least one amino group and an alkenyl group. According to the description, preference is given to fluoranthene derivatives which have at least 5, preferably at least 6, fused rings. These compounds emit light of a longer wavelength, so that yellow to reddish light can be emitted. The fluoranthene derivatives disclosed in EP-A 1 138 745 preferably bear an amino group to increase the life of the fluoranthene derivatives.

US 2002/0022151 A1 likewise relates to OLEDs which comprise specific fluoranthene compounds as light-emitting material. These fluoranthene compounds have at least one diarylamino group.

JP-A 10-169992 relates to benzofluoranthene derivatives and their use in, inter alia, organic light-emitting diodes. The benzofluoranthene derivatives of JP-A 10-169992 display an absorption maximum at about 410 nm, i.e. in the blue-violet region.

It is an object of the present invention to provide compounds which are suitable as emitter molecules in OLEDs, have a long life, are highly efficient in OLEDs, have an emission maximum in the blue region and display a high quantum yield.

This object is achieved by fluoranthene derivatives of the general formula I

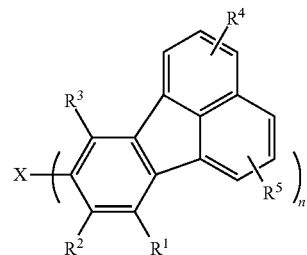

where the symbols have the following meanings:
$R^1$, $R^2$, $R^3$, $R^4$, $R^5$ are each hydrogen, alkyl, an aromatic radical, a fused aromatic ring system, a heteroaromatic radical or —CH=CH$_2$, (E)- or (Z)—CH=CH—C$_6$H$_5$, acryloyl, methacryloyl, methylstyryl, —O—CH=CH$_2$ or glycidyl;
where at least one of the radicals $R^1$, $R^2$ and/or $R^3$ is not hydrogen;
X is alkyl, an aromatic radical, a fused aromatic ring system, a heteroaromatic radical or a radical of the formula (I')

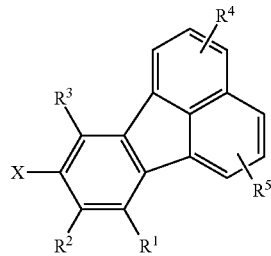

or an oligophenyl group;
n is from 1 to 10 or, in the case of X=oligophenyl group, 1-20;
with the proviso that $R^1$, $R^2$, $R^3$ and X are not at the same time phenyl when $R^4$ and $R^5$ are hydrogen.

The fluoranthene derivatives of the invention bear substituents which are linked to the fluoranthene skeleton via a C—C single bond. Surprisingly, the fluoranthene derivatives of the invention are sufficiently stable for them to be used in a light-emitting layer in OLEDs having a long life. Furthermore, the compounds of the invention have a very high stability toward photooxidation when used in OLEDs.

It has surprisingly been found that the fluoranthene derivatives of the invention emit light in the blue region of the visible electromagnetic spectrum. This means that the fluoranthene derivatives of the invention generally emit light in the region of the visible electromagnetic spectrum from 430 to 480 nm, preferably from 440 to 470 nm, particularly preferably from 450 to 470 nm.

To produce displays which encompass the colors of the entire visible spectrum, it is necessary to provide OLEDs which emit light in the red region of the visible electromagnetic spectrum, OLEDs which emit light in the green region of the visible electromagnetic spectrum and OLEDs which emit light in the blue region of the visible electromagnetic spectrum. It has been found that the provision of efficient OLEDs which emit light in the blue region of the visible electromagnetic spectrum is particularly problematical.

The fluoranthene derivatives of the invention are suitable for producing OLEDs which emit light in the blue region of the visible electromagnetic spectrum.

For the purposes of the present patent application, the term "alkyl" refers to a linear, branched or cyclic, substituted or unsubstituted $C_1$-$C_{20}$—, preferably $C_1$-$C_9$-alkyl group. If X and $R^2$ are an alkyl group, this is preferably a linear or branched $C_3$-$C_{10}$—, particularly preferably $C_5$-$C_9$-alkyl group. The alkyl groups can be unsubstituted or be substituted by aromatic radicals, halogen, nitro, ether or carboxyl groups. The alkyl groups are particularly preferably unsubstituted or substituted by aromatic radicals. Preferred aromatic radicals are specified below. Furthermore, one or more nonadjacent carbon atoms of the alkyl group which is/are not bound directly to the fluoranthene skeleton can be replaced by Si, P, O or S, preferably by O or S.

For the purposes of the present patent application, the term "aromatic radical" preferably refers to a $C_6$-aryl group (phenyl group). This aryl group can be unsubstituted or be substituted by linear, branched or cyclic $C_1$-$C_{20}$—, preferably $C_1$-$C_9$-alkyl groups which may in turn be substituted by halogen, nitro, ether or carboxyl groups or by one or more groups of the formula I'. Furthermore, one or more carbon atoms of the alkyl group can be replaced by Si; P, O, S or N, preferably O or S. Furthermore, the aryl groups or the heteroaryl groups can be substituted by halogen, nitro, carboxyl groups, amino groups or alkoxy groups or $C_6$-$C_{14}$—, preferably $C_6$-$C_{10}$-aryl groups, in particular phenyl or naphthyl groups. The term "aromatic radical" particularly preferably refers to a $C_6$-aryl group which may be substituted by one or more groups of the formula I', by halogen, preferably Br, Cl or F, amino groups, preferably NAr'Ar", where Ar' and Ar" are, independently of one another, $C_6$-aryl groups which, as defined above, can be unsubstituted or substituted and the aryl groups Ar' and Ar" may be substituted by, apart from the abovementioned groups, in each case at least one radical of the formula I; and/or nitro groups. This aryl group is very particularly preferably unsubstituted or substituted by NAr'Ar".

For the purposes of the present patent application, the term "fused aromatic ring system" refers to a fused aromatic ring system which generally has from 10 to 20 carbon atoms, preferably from 10 to 14 carbon atoms. These fused aromatic ring systems can be unsubstituted or be substituted by linear, branched or cyclic $C_1$-$C_{20}$—, preferably $C_1$-$C_9$-alkyl groups which may in turn be substituted by halogen, nitro, ether or carboxyl groups. Furthermore, one or more carbon atoms of the alkyl group can be replaced by Si, P, O, S or N, preferably O or S. Furthermore, the fused aromatic groups can be substituted by halogen, nitro, carboxyl groups, amino groups or alkoxy groups or $C_6$-$C_{14}$—, preferably $C_6$— to $C_{10}$-aryl groups, in particular phenyl or naphthyl groups. The term "fused aromatic ring system" preferably refers to a fused aromatic ring system which may be substituted by halogen, preferably Br, Cl or F, amino groups, preferably NAr'Ar", where Ar and Ar' are, independently of one another, $C_6$-aryl groups which, as defined above, may be unsubstituted or substituted and the aryl groups Ar' and Ar" may be substituted by, apart from the abovementioned groups, in each case at least one radical of the formula I', or nitro groups. Very particular preference is given to the fused aromatic ring system being unsubstituted. Suitable fused aromatic ring systems are, for example, naphthalene, anthracene, pyrene, phenanthrene or perylene.

For the purposes of the present patent application, the term "heteroaromatic radical" refers to a $C_4$-$C_{14}$—, preferably $C_4$-$C_{10}$—, particularly preferably $C_4$-$C_5$-heteroaryl group containing at least one N or S atom. This heteroaryl group can be unsubstituted or be substituted by linear, branched or cyclic $C_1$-$C_{20}$—, preferably $C_1$-$C_9$-alkyl groups which may in turn be substituted by halogen, nitro, ether or carboxyl groups. Furthermore, one or more carbon atoms of the alkyl group can be replaced by Si, P, O, S or N, preferably O or S. Furthermore, the heteroaryl groups can be substituted by halogen, nitro, carboxyl groups, amino groups or alkoxy groups or $C_6$-$C_{14}$—, preferably $C_6$-$C_{10}$-aryl groups. The term "heteroaromatic radical" particularly preferably refers to a heteroaryl group which may be substituted by halogen, preferably Br, Cl or F, amino groups, preferably NArAr', where Ar and Ar' are, independently of one another, $C_6$-aryl groups which, as defined above, may be unsubstituted or substituted, or nitro groups. Very particular preference is given to the heteroaryl group being unsubstituted.

For the purposes of the present patent application, the term "oligophenyl" refers to a group of the general formula (IV)

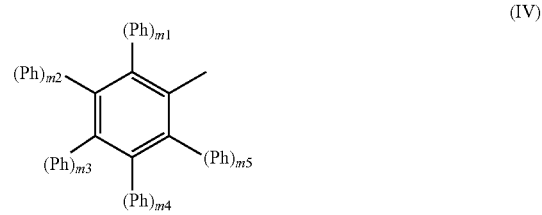

where Ph is in each case phenyl which may in turn be substituted in all 5 substitutable positions by a group of the formula (IV);

$m^1$, $m^2$, $m^3$ $m^4$ and $m^5$ are each, independently of one another, 0 or 1, where at least one index $m^1$, $m^2$, $m^3$, $m^4$ or $m^5$ is at least 1.

Preference is given to oligophenyls in which $m^1$, $m^3$ and $m^5$ are each 0 and $m^2$ and $m^4$ are each 1 or oligophenyls in which $m^1$, $m^2$, $m^4$ and $m^5$ are each 0 and $m^3$ is 1, and also oligophenyls in which $m^2$ and $m^4$ are each 0 and $m^1$, $m^5$ and $m^3$ are each 1.

The oligophenyl group can thus be a dendritic, i.e. hyperbranched, group, in particular when $m^1$, $m^3$ and $m^5$ are each 0 and $m^2$ and $m^4$ are each 1 or when $m^2$ and $m^4$ are each 0 and $m^1$, $m^3$ and $m^5$ are each 1 and the phenyl groups are in turn substituted in from 1 to 5 of their substitutable positions by a group of the formula (IV), preferably in 2 or 3 positions, particularly preferably, in the case of substitution in 2 positions, in each case in the meta position relative to the point of linkage to the base structure of the formula (IV) and, in the case of substitution in 3 positions, in each case in the ortho position and in the para position relative to the point of linkage to the base structure of the formula (TV).

However, the oligophenyl group can also be essentially unbranched, particularly when only one of the indices $m^1$, $m^2$, $m^3$, $m^4$ and $m^5$ is 1, with preference being given to $m^3$ being 1 and $m^1$, $m^2$, $m^4$ and $m^5$ being 0 in the unbranched case. The phenyl group can in turn be substituted in from 1 to 5 of its substitutable positions by a group of the formula (IV); the phenyl group is preferably substituted in one of its substitutable positions by a group of the formula (IV), particularly preferably in the para position relative to the point of linkage to the base structure. Hereinafter, the substituents linked directly to the base structure will be referred to as first substituent generations. The group of the formula (IV) can in turn be substituted as defined above. Hereinafter, the substituents linked to the first substituent generation will be referred to as second substituent generation.

Any desired number of further substituent generations analogous to the first and second substituent generations are possible. Preference is given to oligophenyl groups having the abovementioned substitution patterns and having a first substituent generation and a second substituent generation or oligophenyl groups which have only a first substituent generation.

For the purposes of the present patent application, the term "oligophenyl group" also refers to groups which are based on a base structure of one of the formulae V, VI and VII:

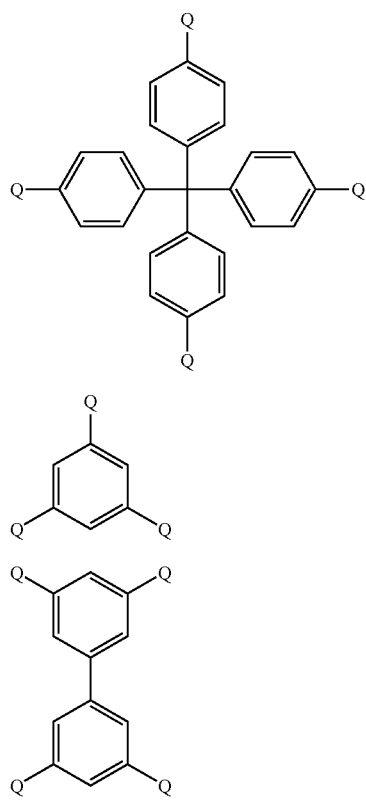

where Q is in each case a bond to a radical of the formula I' or a group of the formula VIII:

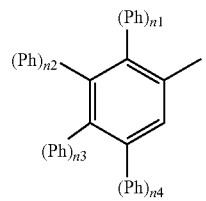

where Ph is in each case phenyl which may in turn be substituted by a group of the formula VIII in a maximum of four positions corresponding to the substitution pattern of the central phenyl ring of the group of the formula VIII;

$n^1$, $n^2$, $n^3$ and $n^4$ are each, independently of one another, 0 or 1, with $n^1$, $n^2$, $n^3$ and $n^4$ preferably being 1.

The oligophenyl groups of the formulae V, VI and VII can thus be dendritic, i.e. hyperbranched, groups.

The oligophenyls of the formulae IV, V, VI and VII are substituted by from 1 to 20, preferably from 4 to 16, particularly preferably from 4 to 8, radicals of the formula (I'), where one phenyl radical can be substituted by one, no or a plurality of radicals of the formula (I'). A phenyl radical is preferably substituted by one or no radical of the formula (I'), with at least one phenyl radical being substituted by a radical of the formula (I').

Very particularly preferred compounds of the formula I in which X is an oligophenyl radical of the general formula IV are shown below:

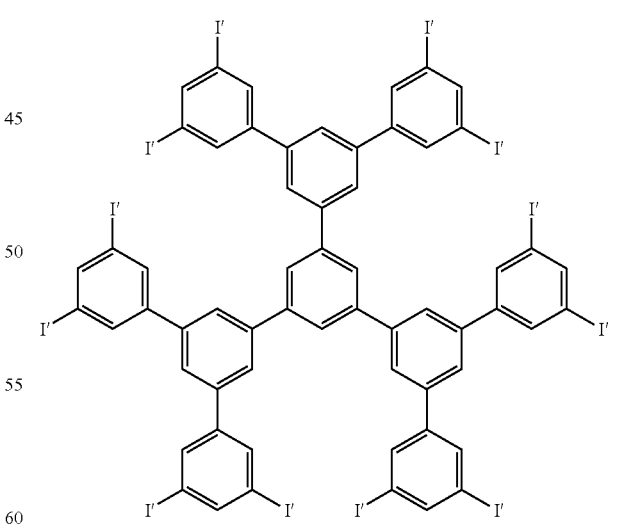

Very particularly preferred compounds of the formula I in which X is an oligophenyl radical of the general formula V, VI or VII are shown below:

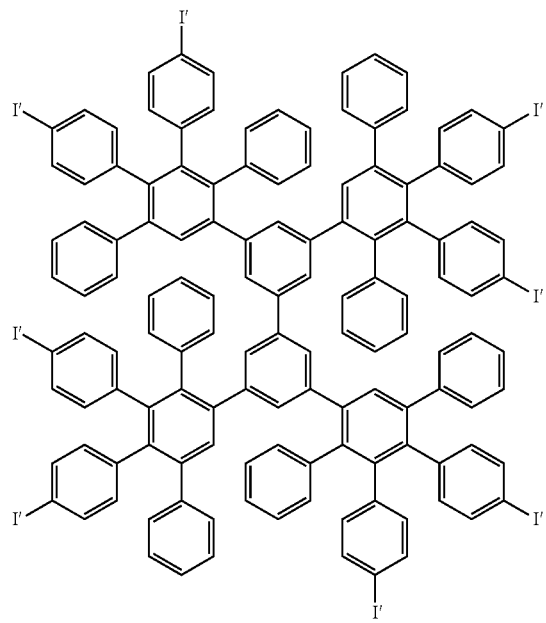

X

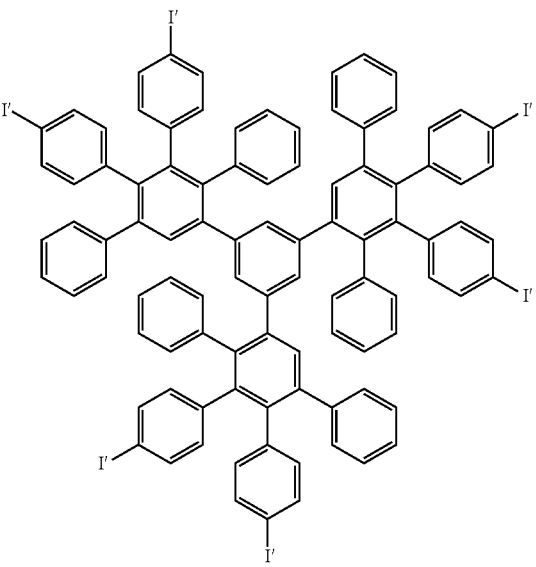

XI

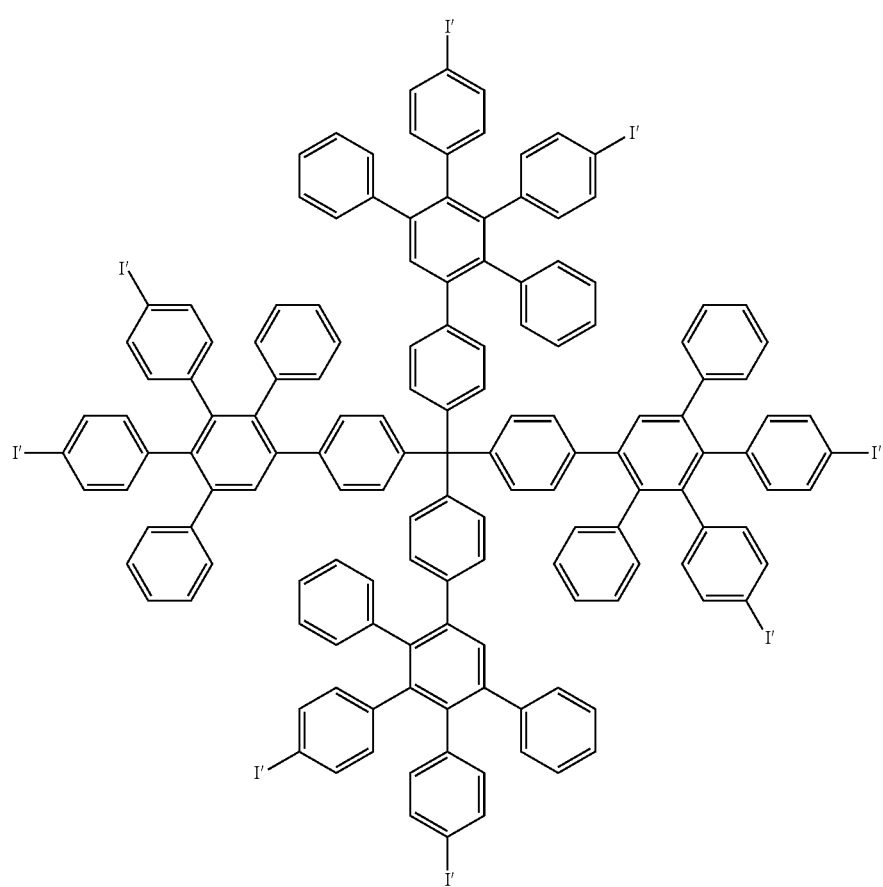

XII

The radicals $R^1$, $R^2$, $R^3$, $R^4$, $R^5$ and X can be selected independently from among the abovementioned radicals, with the proviso that at least one of the radicals $R^1$, $R^2$ and/or $R^3$ is not hydrogen and $R^1$, $R^2$, $R^3$ and X are not at the same time phenyl when $R^4$ and $R^5$ are hydrogen.

$R^4$ and $R^5$ are preferably hydrogen.

$R^1$ and $R^3$ are each preferably an aromatic radical, a fused aromatic ring system or a radical of the formula I', particularly preferably an aromatic radical, with preferred embodiments of the aromatic radical having been described above. Very particular preference is given to $R^1$ and $R^3$ being phenyl.

$R^2$ is preferably hydrogen, alkyl, with preferred embodiments of the alkyl radical having been mentioned above, particularly preferably $C_1$-$C_9$-alkyl which is very particularly preferably unsubstituted and linear, an aromatic radical, with preferred aromatic radicals having been mentioned above, particularly preferably a phenyl radical.

X is preferably an aromatic radical, with preferred aromatic radicals having been mentioned above, particularly preferably a $C_6$-aryl radical which, depending on n, is substituted by from one to three fluoranthenyl radicals, or a fused aromatic ring system, with preferred fused aromatic ring systems having been mentioned above, particularly preferably a $C_{10}$-$C_{14}$ fused aromatic ring system, very particularly preferably naphthyl or anthracenyl, with the fused aromatic ring system being substituted, depending on n, by from one to three fluoranthenyl radicals. If X is an aromatic radical having 6 carbon atoms, it is preferably substituted by fluoranthenyl radicals in the 1 and 4 positions or in the 1, 3 and 5 positions. If X is, for example, an anthracenyl radical, this is preferably substituted by fluoranthenyl radicals in the 9 and 10 positions. For the present purposes, fluoranthenyl radicals are groups of the formula I'

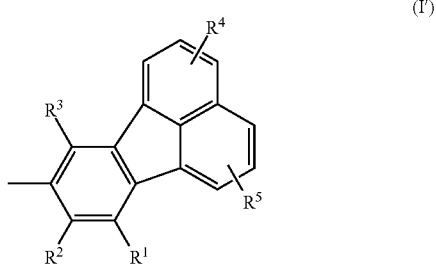

(I')

It is also possible for the radical X itself to be a fluoranthenyl radical of the formula I'.

Furthermore, X can be an oligophenyl group, with preferred oligophenyl groups having been mentioned above. Preference is given to an oligophenyl group of the general formula (IV), where $m^1$, $m^2$, $m^3$, $m^4$ and $m^5$ are each 0 or 1, with at least one of the indices $m^1$, $m^2$, $m^3$, $m^4$ and $m^5$ being 1.

n is an integer from 1 to 10, preferably from 1 to 4, particularly preferably from 1 to 3, very particularly preferably 2 to 3. This means that the fluoranthene derivatives of the general formula I preferably have more than one fluoranthenyl radical of the general formula I'. Preference is thus likewise given to compounds in which X itself is a fluoranthenyl radical. If X is an oligophenyl group, n is an integer from 1 to 20, preferably from 4 to 16.

Very particular preference is given to fluoranthene derivatives of the general formula I which contain no heteroatoms.

In a very particularly preferred embodiment, X is an optionally substituted phenyl radical and n is 2 or 3. This means that the phenyl radical is substituted by 2 or 3 radicals of the formula I'. The phenyl radical preferably contains no further substituents. When n is 2, the radicals of the formula I' are in the para positions relative to one another. If n is 3, the radicals are in the meta positions relative to one another.

In a further preferred embodiment, X is an optionally substituted phenyl radical and n is 1, i.e. the phenyl radical is substituted by one radical of the formula I'.

Preference is also given to X being an anthracenyl radical and n being 2. This means that the anthracenyl radical is substituted by two radicals of the formula I'. These radicals are preferably located in the 9 and 10 positions of the anthracenyl radical.

The preparation of the novel fluoranthene derivatives of the general formula I can be carried out by all suitable methods known to those skilled in the art. In a preferred embodiment, the fluoranthene derivatives of the formula I are prepared by reaction of cyclopentaacenaphthenone derivatives (hereinafter referred to as acecyclone derivatives). Suitable methods of preparing compounds of the formula I in which n is 1 are disclosed, for example, in Dilthey et al., Chem. Ber. 1938, 71, 974, and Van Allen et al., J. Am. Chem. Soc., 1940, 62, 656.

In a preferred embodiment, the novel fluoranthene derivatives of the general formula I are prepared by reacting acecyclone derivatives with alkynyl compounds.

The present invention therefore further provides a process for preparing the fluoranthene derivatives of the invention by reaction of a compound of the formula (II)

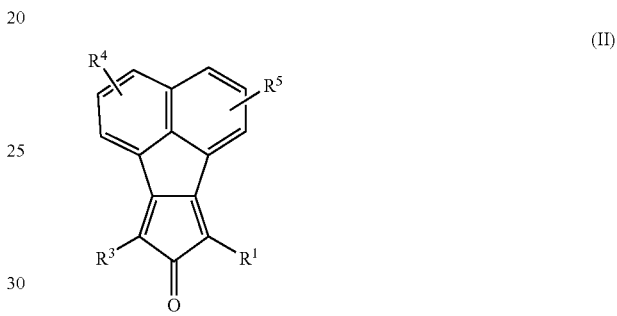

(II)

with an alkynyl compound of the formula (III)

and subsequent elimination of carbon monoxide, where the symbols have the following meanings:

$R^1$, $R^2$, $R^3$, $R^4$, $R^5$ are each hydrogen, alkyl, an aromatic radical, a fused aromatic ring system, a heteroaromatic radical or —CH=CH$_2$, (E)- or (Z)—CH=CH—C$_6$H$_5$, acryloyl, methacryloyl, methylstyryl, —O—CH=CH$_2$ or glycidyl;

where at least one of the radicals $R^1$, $R^2$ and/or $R^3$ is not hydrogen;

X is alkyl, an aromatic radical, a fused aromatic ring system, a heteroaromatic radical or a radical of the formula (I')

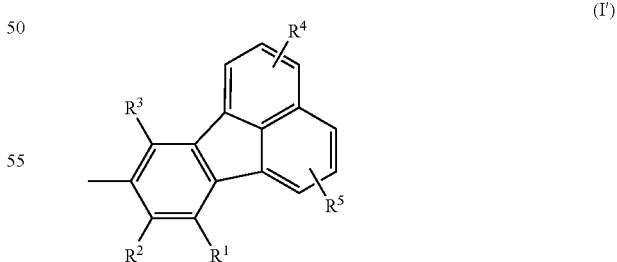

(I')

or an oligophenyl group; and n is from 1 to 10 or, in the case of X=oligophenyl group, from 1 to 20.

The acecyclone derivative of the formula II is prepared by methods known from the prior art, for example by a method in Dilthey et al., J. prakt. Chem. 1935, 143, 189, in which the synthesis of acecyclone (7,9-diphenyl-cyclopenta[a]

acenaphthylen-8-one). Derivatives of acecyclone can be obtained in an analogous manner.

The alkynyl compounds of the formula III can likewise be prepared by methods known to those skilled in the art. Suitable methods are disclosed, for example, in Hagihara et al., Synthesis (1980), 627, and L. Cassar, J. Organomet. Chem. 93 (1979), 253.

The ratio of the acecyclone derivative of the formula II to the alkynyl compound of the formula III is dependent on the number of fluoranthenyl radicals which the desired fluoranthene derivative of the formula I is to bear, i.e. the ratio of acecyclone derivative of the formula II to the alkynyl compound of the formula III is dependent on n. In general, the acecyclone derivative (II) and the alkynyl compound (III) are used in a molar ratio of from n:1 to n+15%:1, preferably from n:1 to n+10%:1. When n=1, an approximately equimolar ratio is preferred, and when n>1, a ratio of acecyclone derivative (II) to alkynyl compound (III) of n+10%: 1 is preferably employed. Suitable values of n have been mentioned above.

In a reaction of acecyclone derivatives of the formula II with an alkynyl compound of the formula III in which n is 1, the reaction is carried out using a molar ratio of the acecyclone derivative of the formula II to the alkynyl compound of the formula III of generally from 1:1 to 1.3:1, preferably from 1:1 to 1.1:1.

In a reaction of the acecyclone derivative of the formula II with an alkynyl compound of the formula III in which n is 2, the reaction is carried out using a molar ratio of the acecyclone compound of the formula II to the alkynyl compound of the formula II of generally from 2:1 to 2.5:1, preferably from 2.1:1 to 2.3:1.

If the acecyclone compound of the formula II is reacted with an alkynyl compound of the formula III in which n is 3, the reaction is carried out using a molar ratio of the acecyclone compound of the formula II to the alkynyl compound of the formula III of generally from 3:1 to 3.5:1, preferably from 3.2:1 to 3.4:1.

Preferred radicals $R^1$, $R^3$, $R^4$ and $R^5$ of the acecyclone derivative of the formula II and preferred radicals X and $R^2$ of the alkynyl compound of the formula III and preferred indices n of the alkynyl compound of the formula III correspond to the preferred radicals $R^1$, $R^2$, $R^3$, $R^4$, $R^5$ and X and the preferred indices n which have been mentioned in respect of the novel fluoranthene derivatives of the general formula I.

In a very particularly preferred embodiment, $R^4$ and $R^5$ are each hydrogen and $R^1$ and $R^3$ are each phenyl. Thus, the acecyclone derivative of the formula II which is used is very particularly preferably acecyclone itself.

Very particularly preferred alkynyl compounds are, for example, those in which n is 1, e.g. 9-nonadecyne, 1-octyne, 1-decyne and 1-octadecyne, those in which n is 2, e.g. 1,4-diethynylbenzene and 9,10-bisphenylethynylanthracene and also 2,4-hexadiyne, and those in which n is 3, e.g. 1,3,5-triethynylbenzene.

If X is an oligophenyl, the alkynyl compounds used are oligophenyl derivatives which bear precisely n free acetylene groups (—C≡C—H).

The reaction in the process of the invention is a Diels-Alder reaction with subsequent elimination of carbon monoxide.

The reaction is generally carried out in a solvent, preferably in an organic nonpolar solvent, particularly preferably in an organic nonpolar solvent having a boiling point which is generally above 100° C., preferably above 140° C., particularly preferably above 260° C.

Suitable solvents are, for example, toluene, xylene, diphenyl ether, methylnaphthalene, mesitylene, glycols and their ethers, decalin and mixtures of the solvents mentioned.

In a preferred embodiment of the process of the invention, the acecyclone derivative of the formula II and the alkynyl compound of the formula III are introduced together into the organic solvent and heated to temperatures of generally from 140 to 260° C., preferably from 140 to 170° C. or from 240 to 260° C. The temperature is dependent on the reactivity of the starting materials. Terminal alkynes ($R^2$=H in the formula (II)) generally react at relatively low temperatures, preferably from 140 to 190° C., particularly preferably from 140 to 170° C., very particularly preferably from 140 to 160° C., while internal alkynes ($R^2 \neq$H in the formula (III)) generally react at higher temperatures, preferably from 190 to 260° C., preferably from 220 to 260° C., particularly preferably from 240 to 260° C. The reaction time is generally from 8 to 30 hours. The reaction time depends on the bulkiness of $R^2$ and on n in the formula III. The reaction time in the case of n=1 is preferably from 8 to 18 hours, particularly preferably from 10 to 16 hours, very particularly preferably from 14 to 16 hours. When n=2, the reaction time is preferably from 18 to 28 hours, particularly preferably from 20 to 26 hours, very particularly preferably from 22 to 26 hours. When n=3, the reaction time is preferably from 24 to 30 hours, particularly preferably from 26 to 30 hours, very particularly preferably from 28 to 30 hours.

The reaction mixture obtained is precipitated in a polar solvent, for example in methanol or ethanol, or, if appropriate, in nonpolar solvents such as cyclohexane. In the case of particularly soluble fluoranthene derivatives, the precipitation step can be omitted. The product obtained is then worked up by methods known to those skilled in the art. The work-up is preferably carried out by column chromatography, particularly preferably on silica gel. As eluant, it is possible to use any suitable eluant or eluant mixture. Very particular preference is given to using an ethyl acetate/cyclohexane mixture.

The novel fluoranthene derivatives of the general formula I which are obtained have an absorption maximum in the ultraviolet region of the electromagnetic spectrum and an emission maximum in the blue region of the electromagnetic spectrum. The quantum yield of the fluoranthene derivatives of the invention is generally from 20 to 75% in toluene. It has been found that fluoranthene derivatives of the general formula I in which n is 2 or 3 display particularly high quantum yields of above 50%.

The fluoranthene derivatives of the invention are suitable for emitting electromagnetic radiation in the blue region of the visible electromagnetic spectrum when used in organic light-emitting diodes (OLEDs).

The present invention therefore also provides for the use of fluoranthene derivatives of the general formula (I)

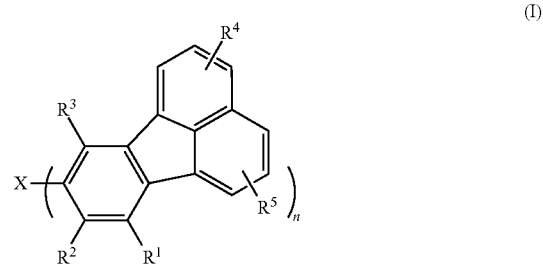

(I)

where the symbols have the following meanings:
$R^1$, $R^2$, $R^3$, $R^4$, $R^5$ are each hydrogen, alkyl, an aromatic radical, a fused aromatic ring system, a heteroaromatic radical or —CH=CH$_2$, (E)- or (Z)—CH=CH—C$_6$H$_5$, acryloyl, methacryloyl, methylstyryl, —O—CH=CH$_2$ or glycidyl;
where at least one of the radicals $R^1$, $R^2$ and/or $R^3$ is not hydrogen;
X is alkyl, an aromatic radical, a fused aromatic ring system, a heteroaromatic radical or a radical of the formula (I')

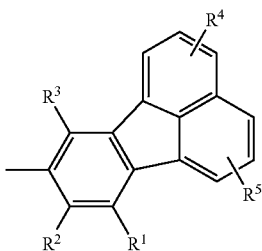

(I')

or an oligophenyl group;
n is from 1 to 10 or, in the case of X=oligophenyl group, from 1 to 20;
as emitter molecule in organic light-emitting diodes (OLEDs). Preferred fluoranthene derivatives and processes for preparing them have been mentioned above.

Organic light-emitting diodes are basically made up of a plurality of layers. Various layer sequences are possible, e.g.:
 anode/hole transport layer/light-emitting layer/cathode;
 anode/light-emitting layer/electron transport layer/cathode;
 anode/hole transport layer/light-emitting layer/electron transport layer/cathode.

The novel fluoranthene derivatives of the general formula I are preferably used as emitter molecules in the light-emitting layer. The present invention therefore also provides a light-emitting layer comprising one or more fluoranthene derivatives of the general formula I

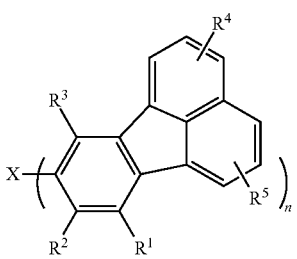

(I)

where the symbols have the following meanings:
$R^1$, $R^2$, $R^3$, $R^4$, $R^5$ are each hydrogen, alkyl, an aromatic radical, a fused aromatic ring system, a heteroaromatic radical or —CH=CH$_2$, (E)- or (Z)—CH=CH—C$_6$H$_5$, acryloyl, methacryloyl, methylstyryl, —O—CH=CH$_2$ or glycidyl;
where at least one of the radicals $R^1$, $R^2$ and/or $R^3$ is not hydrogen;
X is alkyl, an aromatic radical, a fused aromatic ring system, a heteroaromatic radical or a radical of the formula (I')

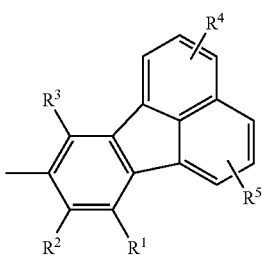

(I')

or an oligophenyl group;
n is from 1 to 10 or, in the case of X=oligophenyl group, from 1 to 20;
as emitter molecule. Preferred fluoranthene derivatives and processes for preparing them have been mentioned above.

The fluoranthene derivatives of the invention can be used in any of the abovementioned layers selected from among the light-emitting layer, the electron transport layer and the hole transport layer. The fluoranthene derivatives of the invention are preferably used as emitters in the light-emitting layer. In the light-emitting layer, the fluoranthene derivatives are preferably used as such, i.e. without addition of further substances. However, it is also possible to use customary light-emitting materials, dopants, hole-transporting substances and/or electron-transporting substances in addition to the fluoranthene derivatives of the invention. If the fluoranthene derivatives of the invention are not used as such, they can be introduced into any of the abovementioned layers in a concentration of from 1 to 70% by weight, preferably from 1 to 20% by weight.

The individual abovementioned layers of the OLEDs can in turn be made up of two or more layers. For example, the hole transport layer can be made up of a layer into which holes are injected from the electrode, hereinafter referred to as hole injection layer, and a layer which transports holes away from the hole injection layer to the light-emitting layer. This layer will hereinafter be referred to as hole transport layer. The electron transport layer can likewise consist of a plurality of layers, e.g. a layer into which electrons are injected by the electrode, hereinafter referred to as electron injection layer, and a layer which receives electrons from the electron injection layer and transports them into the light-emitting layer, hereinafter referred to as electron transport layer. Each of these layers is selected according to factors such as energy level, heat resistance and charge carrier mobility, and also energy difference between the layers mentioned and the organic layers or the metal electrodes.

Suitable materials which can be used as base material in combination with the novel fluoranthene derivatives of the general formula I in the light-emitting layer are anthracene, naphthalene, phenanthrene, pyrene, tetracene, corenene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzooxazoline, bisstyryl, pyrazine, cyclopentadiene, metal complexes of quinoline, metal complexes of aminoquinoline, metal complexes of benzoquinoline, imine, diphenylethylene, vinylanthracene, diaminocarbazole, pyran, thiopyran, polymethine, merocyanine, chelates of oxinoid compounds with imidazoles, quinacridone, rubrene, stilbene derivatives and fluorescent pigments.

As hole-transporting material, use is generally made of a compound which is capable of taking up the holes from the anode and transporting holes and at the same time is suitable for injecting the holes into the light-emitting layer. Suitable hole-transporting materials are, for example, metal complexes of phthalocyanine, of naphthalocyanine, of porphyrin, pyrazolones, tetrahydroimidazoles, hydrazones, acylhydrazones, polyarylalkanes, thiophenes, tertiary aromatic amines such as triphenylamines of the benzidine type, triphenylamines of the styrylamine type, triphenylamines of the diamine type, derivatives of these compounds, silanamines, in particular silanamines bearing triphenylsilyl groups, and macromolecular compounds such as polyvinylcarbazoles, polyvinylsilanes, polythiophene, poly(p-phenylene) and conductive macromolecules. Particularly preferred hole-transporting materials are disclosed, for example, in EP-A 1 138 745 and Chen et al. Macromol. Symp. 125, 9 to 15 (1997).

Suitable electron-transporting materials are compounds which are capable of transporting electrons and can themselves inject electrons into the light-emitting layer. Suitable electron-transporting materials are, for example, oxazoles, oxadiazoles, triazoles, imidazoles, imidazolones, imidazolethiones, fluoranone, anthraquinone dimethane, diphenoquinone, thiopyran dioxide, perylenetetracarboxylic acid, fluorenylidenemethane, distyrylarylenes, arylenes, coumarins and derivatives of the compounds mentioned and also metal chelates. Particularly useful compounds are AlQ₃ (tris(8-hydroxyquinolato)aluminum), BeBq₂, 1,3,4-oxidazol derivatives (OXDs) such as PBD and 1,2,4-triazoles (TAZs). Further suitable compounds are bis(benzimidazolyl) derivatives of perylenedicarboximide (PD), naphthalenedicarboximide (ND) and thiopyran sulfones (TPS). Preferred electron-transporting materials are disclosed, for example, in EP-A 1 138 745.

To increase the stability of the OLEDs of the invention toward heat, moisture and other influences, the OLED can be protected by a protective layer on the surface of the OLED, with this protective layer being made up of, for example, a resin or silicone oil.

As conductive material which is suitable for the anode of the OLED of the invention, preference is given to using a material which has a work function of $\geq 4$ eV. Suitable materials for the anode are, for example, carbon, vanadium, iron, cobalt, nickel, tungsten, gold, platinum, palladium and alloys of these materials, metal oxides as are used for ITO substrates (ITO=indium-tin oxide) and NESA substrates, e.g. tin oxides and indium oxides, and organic conductive polymers such as polythiophene and polypyrrole.

Suitable conductive materials for the cathode are materials which have a work function of <4 eV. Materials suitable for the cathode are, for example, magnesium, calcium, tin, lead, titanium, yttrium, lithium, ruthenium, manganese, aluminum and alloys of these materials.

The anode and the cathode can, if appropriate, have a multilayer structure consisting of two or more layers.

The OLEDs of the present invention preferably additionally have a layer of a chalcogenide, a metal halide or a metal oxide on the surface of at least one electrode pair. Particular preference is given to applying a layer of a chalcogenide (including an oxide) of a metal, e.g. silicon or aluminum, to the surface of the anode on the side pointing in the direction of the light-emitting layer. A layer of a metal halide or a metal oxide is preferably applied to the surface of the cathode which points in the direction of the light-emitting layer. The two abovementioned layers can improve the stability of the OLED. Preferred materials for the layers mentioned are a mention, for example, in EP-A 1 138 745.

Further preferred embodiments of the individual layers of the OLEDs are likewise described in EP-A 1 138 745.

In general, at least one side of the OLED of the invention is transparent in the wavelength range in which light is to be emitted in order to make efficient light emission possible. The transparent electrode is generally applied by vapor deposition or sputtering. The electrode preferably has a transparency to light of $\geq 10\%$ on the light-emitting side of the OLED. Suitable materials are known to those skilled in the art. For example, glass substrates or transparent polymer films can be used.

The production of the OLEDs of the invention is known to those skilled in the art. It is possible for each layer of the OLED to be produced by a dry process for film formation, e.g. vapor deposition, sputtering, plasma plating or ion plating, or a wet process for film formation, e.g. spin coating, dipping or flow coating. The thickness of the individual layers is not subject to particular restrictions and customary thicknesses are known to those skilled in the art. Suitable thicknesses of the layers are generally in the range from 5 nm to 10 μm. Preference is given to thicknesses of from 10 nm to 0.2 μm. The procedures for carrying out dry processes or wet processes for film formation are known to those skilled in the art.

The present invention thus further provides an OLED comprising a light-emitting layer which comprises one or more fluoranthene derivatives of the general formula (I)

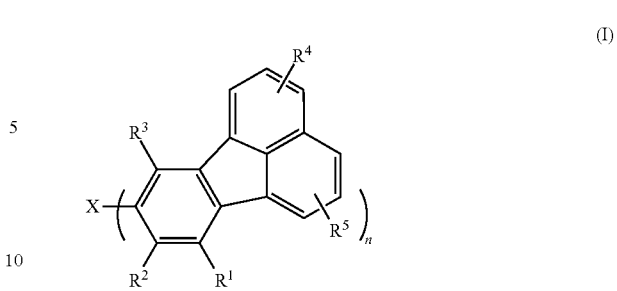

where the symbols have the following meanings:
$R^1$, $R^2$, $R^3$, $R^4$, $R^5$ are each hydrogen, alkyl, an aromatic radical, a fused aromatic ring system, a heteroaromatic radical or —CH=CH₂, (E)- or (Z)—CH=CH—C₆H₅, acryloyl, methacryloyl, methylstyryl, —O—CH=CH₂ or glycidyl;
where at least one of the radicals $R^1$, $R^2$ and/or $R^3$ is not hydrogen;
X is alkyl, an aromatic radical, a fused aromatic ring system, a heteroaromatic radical or a radical of the formula (I')

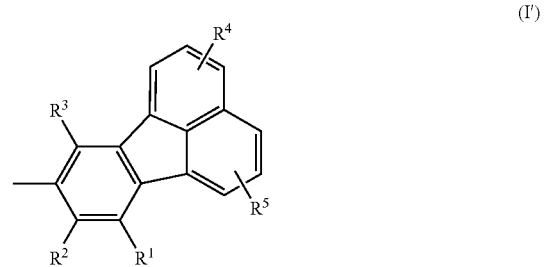

or an oligophenyl group;
n is from 1 to 10 or, in the case of X=oligophenyl group, from 1 to 20;
as emitter molecules. Preferred compounds of the general formula I and processes for preparing them have been mentioned above.

The OLED of the invention can be used in numerous devices. The present invention thus further provides a device selected from the group consisting of stationary VDUs such as VDUs of computers, televisions, VDUs in printers, kitchen appliances and advertising signs, lighting, information signs and mobile VDUs such as VDUs in mobile telephones, laptops, vehicles and also destination displays on buses and trains.

The following examples illustrate the invention.

EXAMPLES 7,8,9,10-Tetraphenylfluoranthene

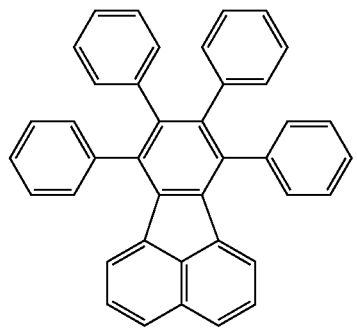

7,8,9,10-Tetraphenylfluoranthene was synthesized as described by Dilthey et al., Chem. Ber. 1938, 71, 974 and Van Allen et al., J. Am. Chem. Soc., 1940, 62, 656.

$\lambda_{max,em}$ (Toluene)=462 nm, quantum yield (toluene): 35%; $\lambda_{max,em}$ (film)=472 nm 8-Naphthyl-2-yl-7,10-diphenylfluoranthene

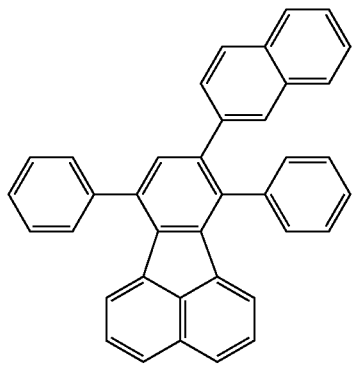

1.281 g of 1-ethynylnaphthalene and 3 g of 7,9-diphenyl-cyclopenta[a]acenaphthylen-8-one (acecyclone, synthesized as described by Dilthey et al., J. prakt. Chem. 1935, 143, 189) were dissolved in 20 g of xylene and refluxed for 16 hours. Precipitation in methanol and chromatography on silica gel (Merck silica gel 60, ethyl acetate/cyclohexane) gave 3.1 g of a beige solid.

$\lambda_{max,em}$ (toluene)=468 nm, quantum yield (toluene): 31%, $\lambda_{max,em}$ (film)=466 nm 8-Nonyl-9-octyl-7,10-diphenylfluoranthene

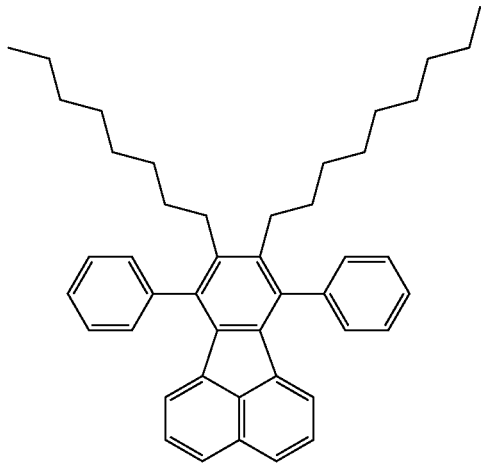

1.484 g of 9-nonadecyne and 2 g of acecyclone were dissolved in 15 g of diphenyl ether and refluxed for 16 hours. Precipitation in methanol and chromatography on silica gel (Merck silica gel 60, ethyl acetate/cyclohexane) gave 8-nonyl-9-octyl-7,10-diphenylfluoranthene as a brownish solid.

$\lambda_{max,em}$ (toluene)=468 nm, quantum yield (toluene): 21%

Benzene-1,4-bis-(2,9-diphenylfluoranth-1-yl)

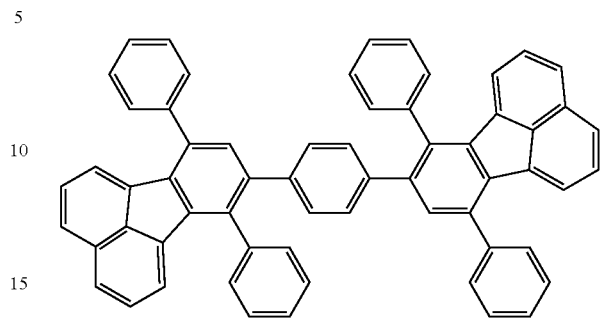

1 g of 1,4-diethynylbenzene and 6.5 g of acecyclone were dissolved in 22 g of xylene and refluxed for 16 hours. Chromatography on silica gel (Merck silica gel 60, ethyl acetate/cyclohexane) gave benzene-1,4-bis(2,9-diphenylfluoranth-1-yl) as a yellowish solid.

$\lambda_{max,em}$ (toluene)=461 nm, quantum yield (toluene): 59%; $\lambda_{max,em}$ (film)=467 nm Benzene-1,3,5-tris(2,9-diphenylfluoranth-1-yl)

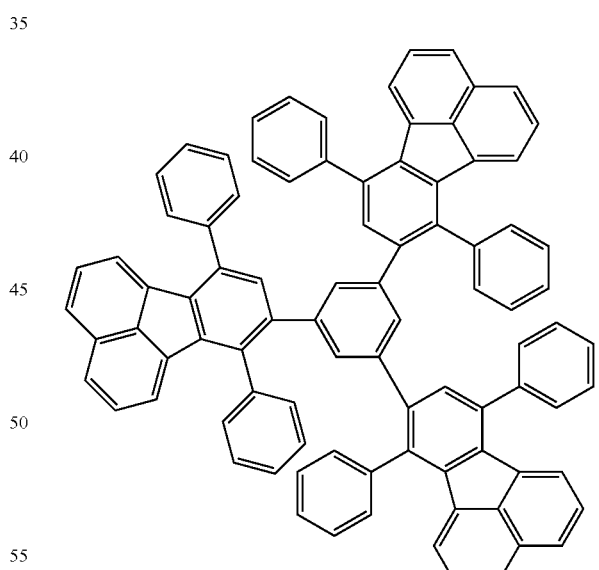

0.2 g of 1,3,5-triethynylbenzene and 2 g of acecyclone were dissolved in 20 g of xylene and refluxed for 24 hours. Precipitation in methanol and filtration through silica gel (Merck silica gel 60, ethyl acetate/cyclohexane) gave 0.6 g of a beige solid.

$\lambda_{max,em}$ (toluene)=459 nm, quantum yield (toluene): 51%; $\lambda_{max,em}$ (film)=467 nm

9,9'-Dimethyl-7,10,7',10''-tetraphenyl-[8,8']bifluoranthene

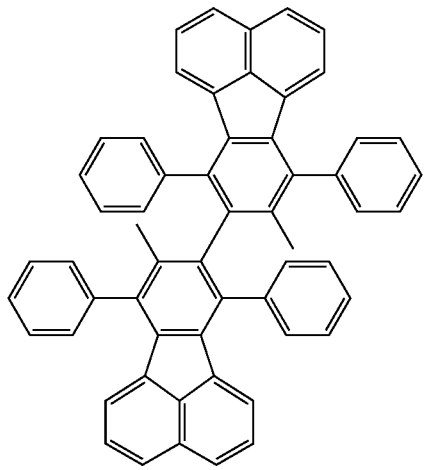

0.61 g of 2,4-hexadiyne and 8 g of acecyclone were dissolved in 15 g of diphenyl ether and refluxed for 26 hours. Distilling off the solvent and chromatography on silica gel (Merck silica gel 60, ethyl acetate/cyclohexane) gave 4.2 g of a beige solid.

$\lambda_{max, em}$ (toluene)=463 nm, quantum yield (toluene): 34%

9,10-Bis(2,9,10-triphenylfluoranthen-1-yl)anthracene, 9,10-bis(9,10-diphenyl-2-octylfluoranthen-1-yl)anthracene

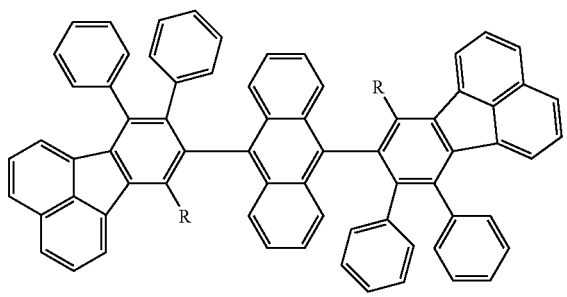

R=phenyl, octyl

Phenyl derivative: 0.92 g of 9,10-bisphenylethynylanthracene and 2 g of acecyclone were dissolved in 15 g of diphenyl ether and refluxed for 14 hours. Distilling off the solvent and precipitation in methanol gave 0.7 g of a gray solid.

$\lambda_{max, em}$ (toluene)=456 nm, quantum yield (toluene): 72%, $\lambda_{max, em}$ (film)=461 nm Alkyl derivative: 0.91 g of 9,10-bis(4-octylphenylethynyl) anthracene (synthesized by double Pd(0)-catalyzed Hagihara-Sonogashira coupling of 1-decyne with 9,10-dibromoanthracene (as described by Hagihara et al., *Synthesis* 1980, 627) and 2.1 g of acecyclone were dissolved in 15 g of diphenyl ether and refluxed for 10 hours. Distilling off the solvent, precipitation in ethanol and chromatography on silica gel (Merck silica gel 60, ethyl acetate/cyclohexane) gave 9,10-bis(9,10-diphenyl-2-octylfluoranthen-1-yl)anthracene (1.8 g).

$\lambda_{max, em}$ (toluene)=455 nm, quantum yield (toluene): 44%

The invention claimed is:

1. A fluoranthene of the general formula I

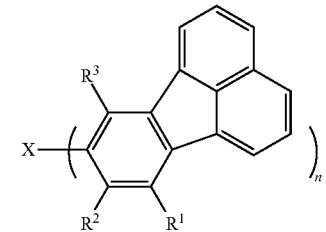

(I)

wherein $R^1$, $R^2$, $R^3$ are each independently hydrogen, alkyl, an aromatic radical, a fused aromatic ring system, or a heteroaromatic radical;
wherein at least one of the radicals $R^1$, $R^2$ and/or $R^3$ is not hydrogen;
wherein
X is an alkyl radical or a radical of the formula (I')

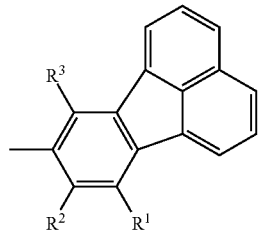

(I')

or an oligophenyl group; and
wherein, when X is a radical of the formula (I'), in the radial of the formula (I'), $R^1$ to $R^3$ have the same meanings as in formula (I);
wherein the oligophenyl group is a group of the general formula (IV)

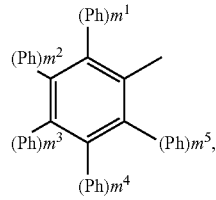

(IV)

wherein Ph is in each case phenyl which, optionally, may be substituted in all 5 substitutable positions by a group of the formula (IV),
wherein, in the oligophenyl group of the general formula (IV), the indexes $m^1$, $m^3$ and $m^5$ are each 0 and $m^2$ and $m^4$ are each 1, or the indexes $m^2$ and $m^4$ are each 0 and $m^1$, $m^3$ and $m^5$ are each 1;
when X is an alkyl radical n is 2 or 3,
when X is a radical of the formula (I') n is 1,
when X is an oligophenyl group n is 1;
with the proviso that $R^1$, $R^2$, $R^3$ and X are not at the same time phenyl.

2. The fluoranthene according to claim 1, wherein $R^1$ and $R^3$ are each a phenyl radical.

3. A fluoranthene of the general formula I

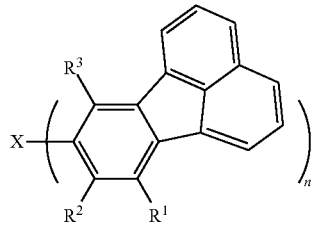

wherein $R^1$, $R^2$, $R^3$ are each independently hydrogen, alkyl, an aromatic radical, a fused aromatic ring system, or a heteroaromatic radical;
wherein at least one of the radicals $R^1$, $R^2$ and/or $R^3$ is not hydrogen;
wherein
X is an alkyl radical, and
n is 2 or 3.

4. An organic light-emitting diode comprising as an emitter molecule a fluoranthene of the general formula (I)

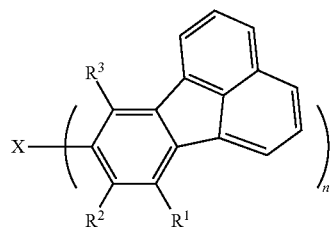

wherein $R^1$, $R^2$, $R^3$ are each independently hydrogen, alkyl, an aromatic radical, a fused aromatic ring system, or a heteroaromatic radical;
wherein at least one of the radicals $R^1$, $R^2$ and/or $R^3$ is not hydrogen;
wherein
X is an alkyl radical or a radical of the formula (I')

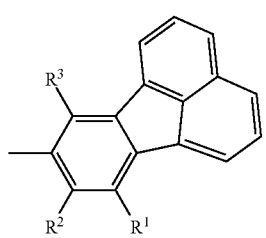

or an oligophenyl group;
wherein, when X is a radical of the formula (I'), in the radial of the formula (I'), $R^1$ to $R^3$ have the same meanings as in formula (I);
wherein the oligophenyl group is a group of the general formula (IV)

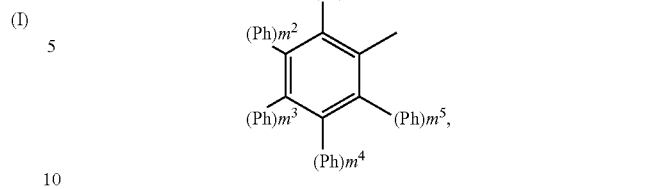

wherein Ph is in each case phenyl which, optionally, may be substituted in all 5 substitutable positions by a group of the formula (IV),
wherein, in the oligophenyl group of the general formula (IV), the indexes $m^1$, $m^3$ and $m^5$ are each 0 and $m^2$ and $m^4$ are each 1, or the indexes $m^2$ and $m^4$ are each 0 and $m^1$, $m^3$ and $m^5$ are each 1; and
when X is an alkyl radical n is 2 or 3,
when X is a radical of the formula (I') n is 1,
when X is an oligophenyl group n is 1.

5. A light-emitting layer comprising one or more floranthenes of the general formula (I) according to claim 1.

6. An organic light-emitting diode (OLED) comprising the light-emitting layer according to claim 5.

7. A device selected from the group consisting of a stationary VDU and a mobile VDU; comprising an OLED according to claim 6.

8. An organic light-emitting diode comprising as an emitter molecule the fluoranthene according to claim 1.

9. A light-emitting layer comprising one or more fluoranthenes of the general formula (I) as defined in claim 2 as emitter molecule(s).

10. An organic light-emitting diode (OLED) comprising the light-emitting layer according to claim 9.

11. A device selected from the group consisting of a stationary VDU and a mobile VDU; comprising the OLED according to claim 10.

12. The device according to claim 7, wherein the device is a stationary VDU, and wherein the stationary VDU is selected from the group consisting of a computer VDU, a television VDU, a printer VDU, a kitchen appliance VDU, an advertising sign VDU, a lighting VDU, and an information sign VUD.

13. The device according to claim 7, wherein the device is a mobile VDU, and wherein the mobile VDU is selected from the group consisting of a mobile telephone VDU, a laptop VDU, a vehicle VDU, a bus destination VDU, and a train destination VDU.

14. The device according to claim 11, wherein the device is a stationary VDU, and wherein the stationary VDU is selected from the group consisting of a computer VDU, a television VDU, a printer VDU, a kitchen appliance VDU, an advertising sign VDU, a lighting VDU, and an information sign VDU.

15. The device according to claim 11, wherein the device is a mobile VDU, and wherein the mobile VDU is selected from the group consisting a mobile telephone VDU, a laptop VDU, a vehicle VDU, a bus destination VDU and a train destination VDU.

16. The device of claim 7, wherein the device is a stationary VDU.

17. The device of claim 7, wherein the device is a mobile VDU.

18. The device of claim 11, wherein the device is a stationary VDU.

* * * * *

UNITED STATES PATENT AND TRADEMARK OFFICE
CERTIFICATE OF CORRECTION

| | |
|---|---|
| PATENT NO. | : 7,906,225 B2 |
| APPLICATION NO. | : 10/573803 |
| DATED | : March 15, 2011 |
| INVENTOR(S) | : Florian Doetz et al. |

It is certified that error appears in the above-identified patent and that said Letters Patent is hereby corrected as shown below:

On the title page, Item (54), and column 1, the title is incorrect. Item (54) and column 1 should read:

-- SYNTHESIS OF PHENYL-SUBSTITUTED FLUORANTHENES BY A DIELS-ALDER REACTION AND THE USE THEREOF --

Signed and Sealed this
Seventh Day of June, 2011

David J. Kappos
*Director of the United States Patent and Trademark Office*